United States Patent [19]

Heath et al.

[11] Patent Number: 5,941,760
[45] Date of Patent: *Aug. 24, 1999

[54] ENDODONTIC INSTRUMENT

[75] Inventors: Derek E. Heath; Jerry A. Mooneyhan, both of Johnson City, Tenn.

[73] Assignee: Dentsply International Inc., York, Pa.

[*] Notice: This patent is subject to a terminal disclaimer.

[21] Appl. No.: 09/119,819

[22] Filed: Jul. 21, 1998

Related U.S. Application Data

[63] Continuation of application No. 09/093,325, Jun. 8, 1998, which is a continuation of application No. 08/890,421, Jul. 9, 1997, Pat. No. 5,762,541, which is a continuation of application No. 08/643,926, May 7, 1996, Pat. No. 5,655,950, which is a continuation of application No. 08/076,367, Jun. 14, 1993, Pat. No. 5,527,205, which is a continuation of application No. 07/787,945, Nov. 5, 1991, abandoned.

[51] Int. Cl.⁶ ..................................................... A61C 1/02
[52] U.S. Cl. ............................... 451/48; 451/28; 433/102
[58] Field of Search ....................... 451/48, 28; 433/102, 433/224, 165, 225

[56] References Cited

U.S. PATENT DOCUMENTS

| | | |
|---|---|---|
| Re. 34,439 | 11/1993 | Heath . |
| 2,797,996 | 7/1957 | Jaffee et al. . |
| 4,197,643 | 4/1980 | Burstone et al. . |
| 4,299,571 | 11/1981 | McSpadden . |
| 4,353,698 | 10/1982 | McSpadden . |
| 4,457,710 | 7/1984 | McSpadden . |
| 4,602,900 | 7/1986 | Arpaio, Jr. et al. . |
| 4,611,509 | 9/1986 | Matsutani . |
| 4,850,867 | 7/1989 | Senia et al. . |
| 4,871,312 | 10/1989 | Heath . |
| 4,894,011 | 1/1990 | Johnson . |
| 4,904,185 | 2/1990 | McSpadden . |
| 4,934,934 | 6/1990 | Arpaio, Jr. et al. . |
| 4,999,952 | 3/1991 | Speiser et al. . |
| 5,035,617 | 7/1991 | McSpadden . |
| 5,065,549 | 11/1991 | Speiser et al. . |
| 5,083,923 | 1/1992 | McSpadden . |
| 5,104,316 | 4/1992 | McSpadden . |
| 5,106,298 | 4/1992 | Heath et al. . |
| 5,125,838 | 6/1992 | Seigneurin . |
| 5,302,129 | 4/1994 | Heath et al. . |
| 5,464,362 | 11/1995 | Heath et al. ............................... 451/48 |
| 5,628,674 | 5/1997 | Heath et al. . |

FOREIGN PATENT DOCUMENTS

| | | |
|---|---|---|
| 3620527 | 12/1997 | Germany . |
| WO 79/00344 | 6/1979 | WIPO . |

OTHER PUBLICATIONS

C. Fuchs et al.; Statistical Models for Evaluating the Penetrating Ability of Endodontic Instruments; J Dent Res 69(9):1617–1621, Sep. 1990.

F. J. Harty et al.; The Giromatic System Compared With Hand Instrumentation in Endodonics; British Dental Journal: 239–244, Sep. 17, 1974.

(List continued on next page.)

*Primary Examiner*—David A. Scherbel
*Assistant Examiner*—Derris Holt Banks
*Attorney, Agent, or Firm*—James B. Bieber

[57] ABSTRACT

A method of fabricating an endodontic instrument by a machining operation is disclosed, and wherein a wire-like rod composed of a titanium alloy is advanced past a rotating grinding wheel at a relatively slow feed rate, with a sufficient depth of cut to remove all of the material on a given surface without over grinding a previously ground surface, and with the grinding wheel rotating at a relatively slow surface speed. The disclosed method is able to efficiently produce endodontic instruments having a high degree of flexibility, high resistance to torsional breakage, and with sharp cutting edges along the working length.

12 Claims, 3 Drawing Sheets

OTHER PUBLICATIONS

William L. Wildey,DDS,BS; E Steve Senia, DS.MS,BS, FACD; A new root canal instrument and instrumentation technique: A preliminary report; Oral Surg. Oral Pathol 1989;67:198–207.

Oscar R. Bolanos, DDS, MS et al.; A Comparison of Engine and Air–Driven Instrumentation Methods with Hand Instrumentation; Journal of Endodontics; vol. 14, No. 8, Aug. 1988, 392–396.

Melvin Goldman, DDS et al.; An In Vitro Study of the Pathfinding Ability of a New Automated Handpiece; Journal of Endodontics; vol. 13, No. 9, Sep. 1987; 429–433.

Marwan Abou–Rass, DDS, MDS, PhD et al.; The use of rotary instruments as auxiliary aids to root canal preparation of molars; Journal of Endodontics; vol. 8, No. 2, Feb. 1992; 78–82.

Juan M. Campos, DDS et al.; Comparison of Mechanical and Standard Hand Instrumentation Techniques in Curved Root Canals; Journal of Endodontics; vol. 16, No. 5, May 1990; 230–234.

Howard Martin, D.M.D. et al.; A quantitative comparison of the ability of diamond and K–type files to remove dentin; Oral Surg Oral Med Oral Pathol; Dec. 1980; vol. 50; No. 6: 566–568.

James A. Gilles, DDS, MS et al.; A Comparison of the Canal Master Endodontics Instrument and K–Type Files for Enlargement of Curved Root Canals: vol. 16, No. 12, Dec. 1990: 561–565.

Garry L. Myers, DDS et al.: A comparison of Weights of Debris Extruded Apically by Conventional Filing and Canal Master Techniques; Journal of Endodontics; vol. 17, No. 6, Jun. 1991: 275–279.

Dennis A. Leseberg, DDS et al.; The Effects of Canal Master, Flex–R, and K–Flex Instrumentation on Root Canal Configuration; Journal of Endodontics; vol.17, No. 2, Feb. 1991; 59–65.

H. Besse et al.; An Evaluation of Four Methods of Root Canal Preparation Using $^{14}$C Urea; Journal of Endodontics; vol. 17, No. 2, Feb. 1991: 54–58.

Thomas Turek, DMD et al.; A light microscopic study of the efficacy of the telescopic and the Giromatic preparation of root canals; Journal of Endodontics; vol. 8, No. 10, Oct. 1982: 437–443.

Steven M. Klayman, DDS, MS et al.; A comparison of the efficacy of serial preparation versus Giromatic preparation; Journal of Endodontics; vol. 1, No. 10, Oct. 1975: 334–337.

F.J. Harty B.D.Sc., L.D.S. et al.; A Comparison of the Flexibility of Giromatic and Hand Operated Instruments in Endodontics; pp. 64–71.

Alfred L. Frank, D.D.S.; An evalution of the Giromatic endodontic handpiece; O.S., O.M. & O.P., Sep. 1967; vol. 24, No. 3: 419–421.

Joseph W. Lehman, III, D.D.S. et al.; An evaluation of a new mechanized endodontic device: The Endolift; Oral Surg, Apr. 1982; vol. 53, No. 4; pp. 417–424.

Juan H. Gutiérrez, D.D.S. et al.; Microscopic and macroscopic investigation on results of mechanical preparation of root canals; O.S., O.M. & O.P., Jan. 1968; vol. 25, No. 1: 108–116.

Samuel Luks, D.D.S.; Power Vs. Hand Instrumentation In Endodontics; NYS Dental Journal, Jun./Jul. 1986: 27–29.

S. Spyropoulos et al.; The effect of Giromatic files on the preparation shape of severely curved canals; International Endodontic Journal (1987) 20, 133–142.

George Weisz; A clincial study using automated instrumentation in root canal therapy; International Endodontic Journal (1985) 18, 203–209.

B. Ciucchi et al.; Comparison of curved canal shape using filing and rotational instrumentation techniques; International Endodontic Journal (1990) 23, 139–147.

Noel R. Ianno, DDS et al.; Article 5; Canal Preparation Using Two Mechanical Handpieces: Distortions, Ledging, and Potential Solutions; Compend Contin Educ Dent, vol. X, No. 2; 100–105.

Olav Molven; Engine and Hand–Operated Root Canal Exploration; From the University of Bergen, School of Dentistry, Institute of Cariology; 61–70.

Arpaio, Jerry; Deposition Transcript of Feb. 6, 1997, pp. 1–210 and Exhibits; Civil Action No.96–272 (MMS).

Heath, Derek Edward Deposition Transcripts of Feb. 27, 1997, pp. 540–666; Jun. 19, 1997, pp. 667–952; and Jun. 20, 1997, pp. 953–1175 and Exhibits; Civil Action No. 96–272 (MMS).

Mooneyhan, Dr. Jerry A. Deposition Transcripts of Mar. 6, 1997, pp. 1–172; Feb. 19, 1997, pp. 1–166; and Mar. 7, 1997, pp. 1–73 and Exhibits; Civil Action No. 96–272 (MMS).

J. Dental Research, vol. 68, Special Issue Abstracts of Papers of 18th Annual Session American Issue of Dental Research, Mar. 15–19, 1989; Abstract of Program 1644 at p. 387.

Machining Data Handbook, Mechinability Data Center Institute of Advanced Manuf. Sciences Inc. 3rd Ed. vol. 2 Chapters 8, 18 and 20 (1980).

Civjan et al.; Potential Applications of Certain Nickel–Titanium (Nitinol) Alloys; J Dent Res Jan.–Feb. 1974; vol. 54 No. 1; pp. 89–96.

M. Field; Plastically Deformed Debris and Built–Up Edge Produced on Surfaces by Chip Removal and Abrasive Machining Processes; Annals of the CIRP, vol. 23/Jan. 1974; pp. 191–192.

P.A. Clorite and E.C. Reed; Influence of Various Grinding Conditions Upon Residual Stresses in Titanium; Transactions of the ASME, Feb., 1958; pp. 297–301.

L. P. Tarasov; How To Grind Titanium; American Machinst, Special Report No. 322; Nov. 10, 1952; pp. 135–146.

Walia, et al.; An Initial Investigation of the Bending and Torsional Properties of Nitinol Root Canal Files; Journal of Endodontics; Jul. 1988, vol. 14, No. 7, pp. 346–351.

Superelastic Ni–Ti Wire, Wire Journal International, Mar. 1991, pp 45–50.

RMI Titanium, RMI Company, Niles, Ohio, 27 pages.

The Grinding Wheel, Lewis and Schleicher, Third Edition, The Grinding Wheel Institute, pp. 382–383.

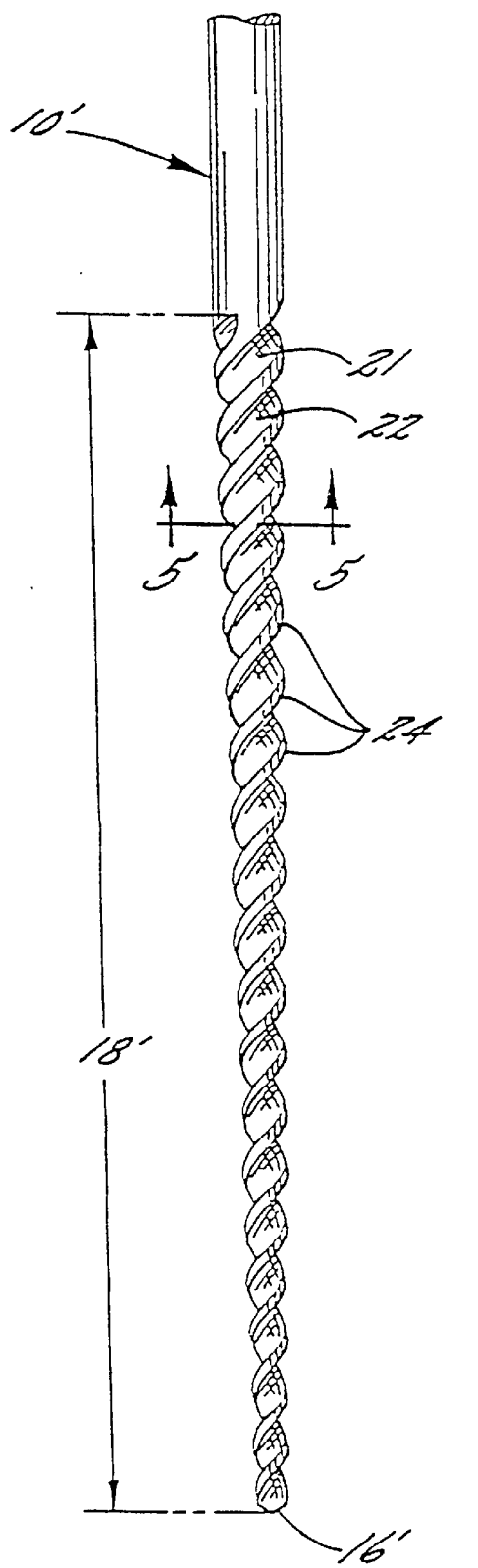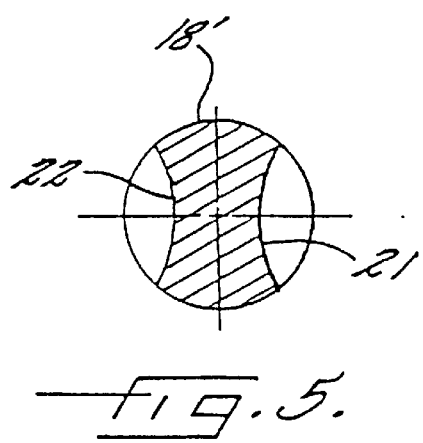
Fig. 4.
Fig. 5.

1. TABLE ADVANCED
2. TABLE LATERALLY WITHDRAWN
3. TABLE RETURNED
4. TABLE LATERALLY RETURNED AND ROD INDEXED

ENDODONTIC INSTRUMENT

This application is a continuation of application Ser. No. 09/093,325, filed Jun. 8, 1998; which is a continuation of application Ser. No. 08/890,421, filed Jul. 9, 1997, now U.S. Pat. No. 5,762,541; which is a continuation of patent application Ser. No. 08/643,926, filed May 7, 1996, now U.S. Pat. No. 5,655,950; which is a continuation of patent application Ser. No. 08/076,367, filed Jun. 14, 1993, now U.S. Pat. No. 5,527,205; which is a continuation of application Ser. No. 07/787,945, filed Nov. 5, 1991, now abandoned.

BACKGROUND OF THE INVENTION

The present invention relates to an endodontic instrument and to a method of fabricating an endodontic instrument adapted for use in performing root canal therapy on teeth, and which is characterized by high flexibility and high resistance to torsional breakage.

Root canal therapy is a well-known procedure wherein the crown of a diseased tooth is opened so as to permit the canal to be cleaned and then filled. More particularly, a series of very delicate, flexible, finger-held instruments or files are used to clean out and shape the root canal, and each file is manually rotated and reciprocated in the canal by the dentist. Files of increasingly larger diameter are used in sequence, to achieve the desired cleaning and shaping. When the canal is thus prepared, it is solidly filled with a filling material, which typically comprises a waxy, rubbery compound known as gutta percha. In one procedure, the gutta percha is positioned on an instrument called a compactor, and the coated compactor is inserted into the prepared canal and rotated and reciprocated to compact the gutta percha therein. The dentist thereafter fills the tooth above the gutta percha with a protective cement, and lastly, a crown is fitted to the tooth.

Endodontic instruments of the described type are conventionally fabricated by permanently twisting a stainless steel rod of triangular or square cross section. The apices of the triangular or square cross section thus form cutting edges which spiral along the length of the instrument. More recently, such instruments have been produced by a machining process, and wherein a cylindrical rod of stainless steel is moved past a rotating grinding wheel, and while the rod is slowly rotated about its axis so as to impart a desired helical configuration to the ground surface and form a spiral flute on the surface. The rod is thereafter indexed and again moved past the wheel, and these steps are repeated as many times as are necessary to form the rod into a triangular or square cross section. By appropriate control of the process, helical lands may be formed between the spiral flutes as illustrated in U.S. Pat. No. 4,871,312 to Heath.

It is well-known by clinicians that inadvertent errors can occasionally arise during root canal therapy as described above. These errors can include the formation of a ledge in the wall of the canal, the perforation of the canal, and a separation or fracture of the instrument. Many of these errors which occur during the therapy of a canal have a common genesis, i.e. the basic stiffness of the stainless steel instruments, particularly with the respect to the instruments of larger size. Efforts have been made to improve the flexibility of stainless steel instruments based upon different cross sectional shapes, but without significant success.

Recently, a series of comparative tests of endodontic instruments made of nickel-titanium (Nitinol) allay and stainless steel were conducted. The results of the tests were published in an article entitled "An Initial Investigation of the Bending and the Torsional Properties of Nitinol Root Canal Files", *Journal of Endodontics*, Volume 14, No. 7, July 1988, at pages 346–351.

The Nitinol instruments involved in the above tests were machined in accordance with the procedure and operating parameters conventionally used in the machining of stainless steel endodontic instruments. More particularly, this standard procedure involves the following parameters:

1. Feed Rate

The rod from which the instrument is to be formed is moved axially past a rotating grinding wheel at a feed rate of about ten inches per minute. The rod is slowly rotated about its axis as it is axially advanced so as to impart a helical configuration to the ground surface.

2. Depth of Cut

The depth of each cut is sufficient to remove all of the material on a given surface without over grinding a previously ground surface. For example, in the case of an instrument triangular cross-section, the rod is moved past the wheel three times, once for each surface, with about 25 percent of the diameter being removed on each cut.

3. Speed of Wheel

An aluminum oxide grinding wheel is provided which is rotated at a surface speed of about 6000 feet per minute, and the wheel has a grit size of about 220.

The above tests demonstrated that the Nitinol instruments produced by the described machining process exhibited superior flexibility and torsional properties as compared to stainless steel instruments, but the cutting edges of the instruments exhibited heavily deformed metal deposits, which rendered the instruments-generally unsatisfactory for use.

It is accordingly an object of the present invention to provide a method of fabricating an endodontic instrument which is characterized by high flexibility and high resistance to torsional breakage.

It is another object of the present invention to provide a method of efficiently fabricating an endodontic instrument which is composed of a titanium alloy, such as a nickel-titanium alloy, and which exhibits high flexibility and high resistance to torsional breakage, and which is also characterized by sharp cutting edges.

SUMMARY OF THE INVENTION

The above and other objects and advantages of the present invention are achieved in the embodiments illustrated herein by the discovery that when an endodontic instrument of titanium alloy is machined under certain specific operating parameters, a totally satisfactory instrument, having high flexibility, high resistance to torsion breakage, and sharp cutting edges, may be produced. The specific operating parameters are not suggested by the known procedure for machining stainless steel instruments as summarized above, and indeed, the parameters which are effective in producing a satisfactory instrument are directly contrary to accepted practices for machining titanium alloys as presented in authoritative literature, note for example the brochure entitled "RMI Titanium", published by RMI Company of Niles, Ohio.

More particularly, the present invention involves the steps of (a) providing a cylindrical rod of metallic material which is composed of at least about 40% titanium and which has a diameter less than about 0.06 inches, and (b) axially moving the rod past a rotating grinding wheel at a feed rate of not more than about 5 inches per minute, while rotating the rod about its axis, and so that the wheel removes at least about 25% of the diameter of the rod at the point of maximum removal and forms a helical surface on the rod. The grinding wheel is rotated at a relatively slow surface speed of not more than about 3000 feet per minute, and preferably not more than about 2200 feet per minute. Also, the grinding wheel has a relatively fine grit size which is greater than about 200 grit, and preferably greater than about 220 grit. In the preferred embodiment, the rod is composed of an alloy comprising at least about 40% titanium and about 50% nickel.

It is often preferred to form the rod into a triangular or square cross sectional configuration, and in such embodiments, the rod is rotatably indexed about a rotational axis of not more than 180 degrees, and specifically either 120 degrees or 90 degrees, and step (b) is repeated so as to form a second helical surface on the rod. The indexing and grinding stems are again repeated as many times as are necessary to form the desired number of sides on the instrument.

BRIEF DESCRIPTION OF THE DRAWINGS

Some of the objects and advantages of the present invention having been stated, others will appear as the description proceeds, when taken in conjunction with the accompanying drawings, in which

FIG. 4 is a view similar to FIG. 2, but illustrating a second embodiment of the instrument;

FIG. 5 is a transverse sectional view taken substantially along the line 5—5 of FIG. 4;

DETAILED DESCRIPTION OF THE PREFERRED EMBODIMENTS

Figure 1:
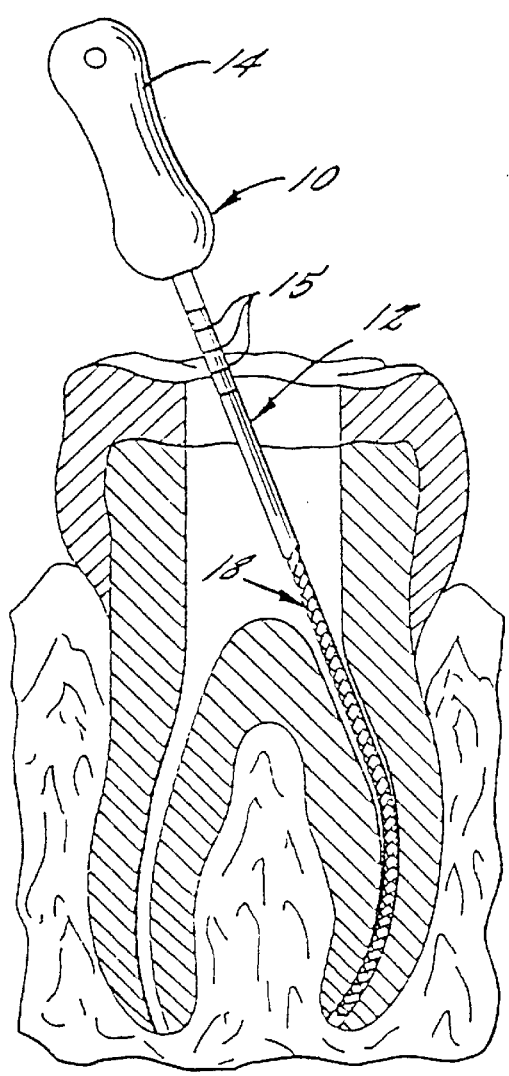
FIG. 1 is a cross sectional view of a tooth have two roots, with an endodontic instrument manufactured in accordance with the present invention being positioned in one of the roots.
Figure 3:
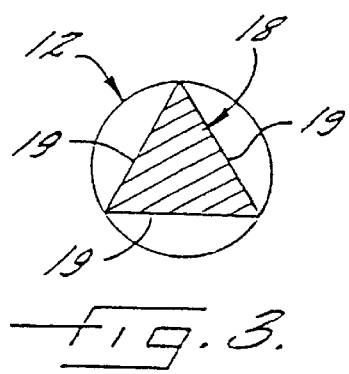
FIG. 3 is a transverse sectional view taken substantially along the line 3—3 of FIG. 2.
Figure 2:
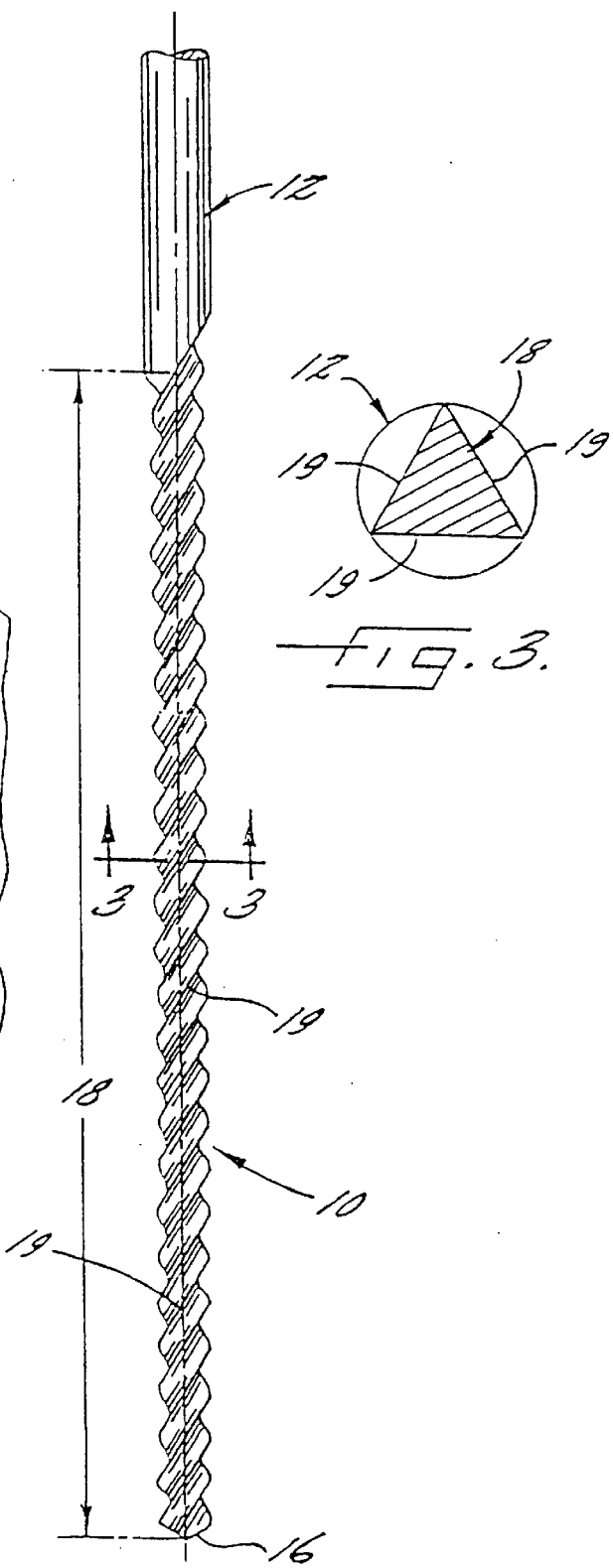
FIG. 2 is an enlarged perspective view of the lower portion of the instrument shown in FIG. 1.

Referring more particularly to FIGS. 1–3, an endodontic instrument 10 is illustrated which comprises a shank 12 which is composed of a titanium alloy as further described below. The shank 12 typically has a length of about 30 mm (1.2 inches), and it includes an outer or proximate end which mounts a conventional handle 14. The portion of the shank immediately below the handle is cylindrical and has a diameter of between about 0.5 and 1.6 mm (0.02 and 0.07 inches), and this shank portion includes calibrated depth markings 15 of conventional design. The shank further includes an opposite distal or pilot end 16, and a working length 18 is defined adjacent the pilot end 16. The working length may be cylindrical as illustrated, or it may be slightly tapered toward the pilot end 16 at an included angle of about one degree. The working length 18 may have a length of about 2 mm (0.08 inches) up to the full length of the shank 12, i.e. about 30 mm (1.2 inches). However, in the illustrated embodiment, the working length 18 has a length sufficient to extend substantially the full depth of a tooth root canal as illustrated in FIG. 1, which is about 16 mm (0.63 inches). Also, the cross sectional configuration of the working length 18 is triangular and is composed of three linear surfaces 19, as best seen in FIG. 3, and so that the apices of the triangle form cutting edges.

FIGS. 4-5 illustrate a second embodiment of an endodontic instrument 10' which may be fabricated in accordance with the present invention. In this embodiment, the outer peripheral surface of the working length 18' is tapered at an included angle of between about ½ and 4 degrees, and preferably of about one degree, and the working length 18' includes two continuous helical flutes 21, 22 formed in the peripheral surface. The flutes are preferably of uniform pitch P (FIG. 4), which is defined herein as the distance between corresponding points of adjacent flute segments. In a typical example, the length of the working length 18 is about 0.63 inches, with a total of about 18 flute spirals extending along the entire length of the pilot end portion, such that the pitch P is 0.63/18 or about 0.035 inches. Since the depth of the flutes varies as described above, the width F of the flutes, and the width L of the lands 30 will inversely vary somewhat along the length of the pilot end portion. For example, in the above example, the width F of the flutes is about 0.03 inches and the width L of lands 30 is about 0.005 inches at the upper end of the working length adjacent the handle 14, and the width W is about 0.025 inches and the width L is about 0.01 inches adjacent the pilot end 16. As will be apparent, the width L of the lands 30 is equal to a significant portion of the pitch P, which is preferably equal to at least about 15% of the pitch P. In the above example, the width L varies from about 14.2% of the pitch P adjacent the upper end to about 28.5% of the pitch P adjacent the pilot end 16. This is desirable in that the relatively broad lands 30 prevent undue cutting by the instrument laterally into the wall of the canal during manipulation of the instrument by the dentist. The flutes have an arcuate curvature as best seen in FIG. 5, and they have a pitch so as to define helical lands 24 on the outer periphery of the instrument. The shank 12 above the working portion 14 is shown as being substantially cylindrical. A fitting 18 is attached to the upper cylindrical part of the shank 12 which is adapted to mate with a chuck of a dental handpiece (not shown). An instrument of this general construction is further described in U.S. Pat. No. 4,871,312 to Heath, and pending application Ser. No. 07/679,628, filed Apr. 3, 1991.

Figure 6:
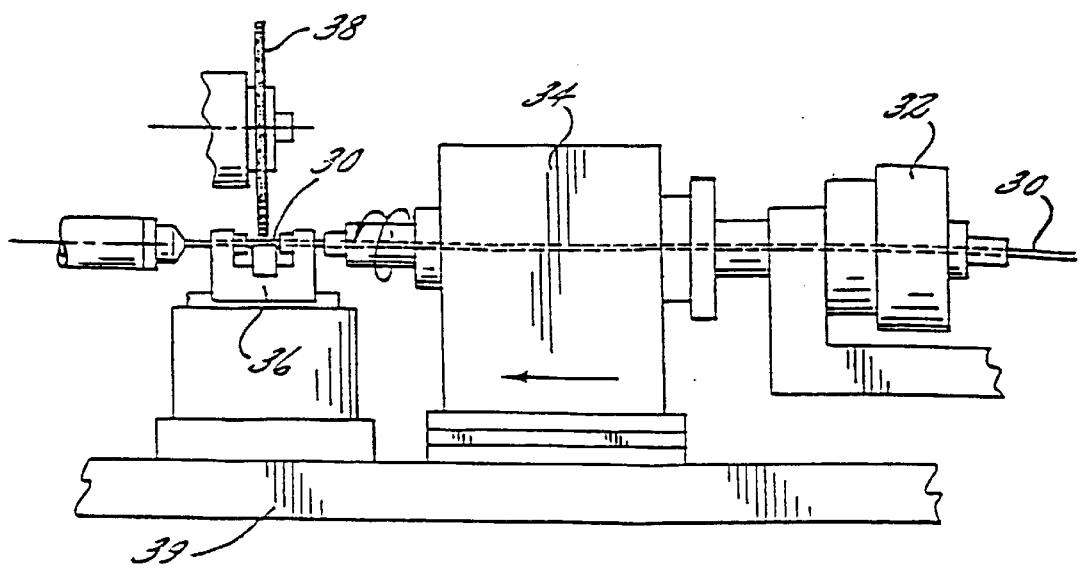
FIG. 6 is a schematic side elevation view of a machining apparatus which is adapted to fabricate endodontic instruments in accordance with the present invention.
Figure 7:
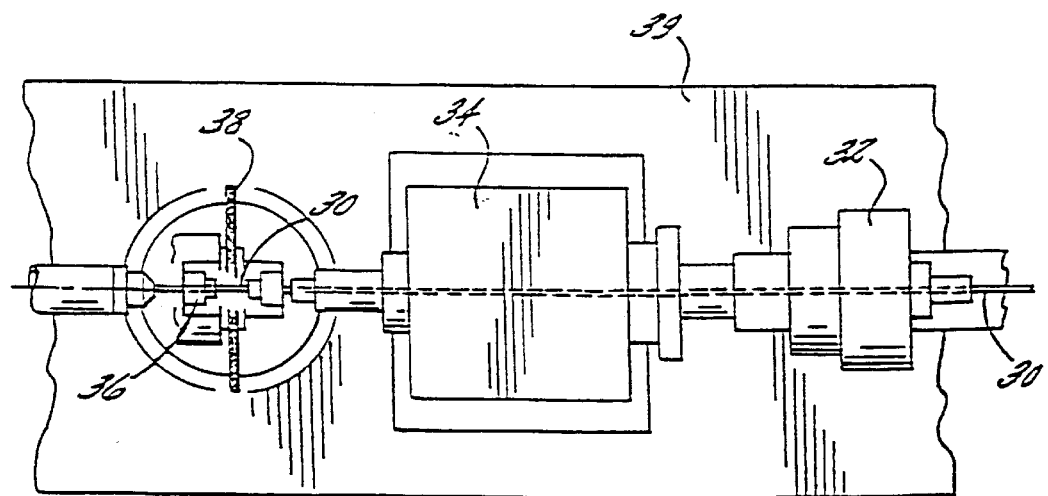
FIG. 7 is a top plan view of the apparatus shown in FIG. 6, and illustrating certain of the steps of the fabrication process.

FIGS. 6 and 7 schematically illustrate a machining apparatus for practicing the method of the present invention. As will be further described below, the method involves a unique machining process which has been found to efficiently produce endodontic instruments of the type described, from a rod 30 composed of titanium alloy. Such alloys typically have a titanium content of at least about 40 percent. Nickel-titanium alloys are preferred, which typically consist of about 40 percent titanium and about 50 percent nickel. In one preferred specific embodiment, the alloy consists of 44 percent titanium and 56 percent nickel and no appreciable amount of other ingredients which could adversely effect the purity required for endodontic instruments.

The rod 30 from which the instrument is to be fabricated is conventionally supplied from the producer in a selected diameter, which closely conforms to the diameter of the instrument being produced. In this regard, endodontic instruments are sized in accordance with established standards, which range from a diameter at the pilot end 16 of 1.4 mm (0.062 inches—size 140) to a diameter at the pilot end 16 of 0.06 mm (0.0024 inches—size 06).

In accordance with the illustrated embodiment of the present invention, the continuous rod 30 is positioned to extend through an axial feed block 32 and an indexing block 34 of conventional well-known construction. A work holding fixture 36 is positioned to support the forward end of the rod 30 adjacent the periphery of a rotating grinding wheel 38. The two blocks 32, 34 are then advanced so that the rod 30 is axially moved past the rotating grinding wheel 36 at a slow feed rate of between about 3 to 8 inches per minute, and preferably not more than about 5 inches Per minute. Concurrently with this axial movement, the indexing block 34 serves to slowly rotate the rod 30 about its axis at a controlled speed, which causes the ground surface 19 to assume a helical configuration as described above with respect to FIGS. 2 and 3.

The rod preferably moves past the wheel only once for each ground surface 19, and thus the rod is positioned with respect to the wheel 38 such that the full depth of the cut is removed in a single pass. As best seen in FIG. 3, the wheel preferably removes at least about 25 percent of the diameter of the rod at the point of maximum removal, which is along a diameter which extends perpendicular to the surface 19 being formed.

As a further aspect of the present invention, the grinding wheel 38 is rotated at a relatively slow surface speed of not more than about 3000 feet per minute, and preferably not more than about 2200 feet per minute. Further, the wheel 38 is composed of a relatively fine grit, which is greater than about 200 and preferably about 220 grit. A wheel of the above grit size and which is fabricated from silicon carbide has been found to be very satisfactory.

To produce an instrument of the construction illustrated in FIGS. 1–3, the grinding wheel 38 is oriented to rotate about an axis generally parallel to the axis of the advancing rod 30, and the wheel 38 thus forms a generally flat surface 19. Also, by reason of the slow rotation of the rod about its axis, this flat surface assumes a helical configuration. Where the instrument is to have a tapered working length, the axis of the index block 34 is slightly inclined with respect to the rotational axis of the wheel 38, so as to provide a controlled and variable depth of cut along the working length.

When the rod 30 has advanced past the rotating wheel 38 a distance sufficient to form the first surface 19 along the desired working length on the instrument, the table 39 supporting the feed block 32, the index block 34, and the fixture 36 is moved laterally, then axially rearwardly, and then laterally back to its original position as illustrated schematically in FIG. 7. Concurrently, the rod 30 is rotatably indexed about its axis. The angular extent of this rod indexing will depend upon the number of surfaces 19 desired on the finished instrument, and where three surfaces are to be formed as seen in FIG. 3, the rod is indexed 120 degrees. The rod is then again axially advanced while being slowly rotated, and so as to form the second surface 19. The table 39 is then again moved laterally and rearwardly in the manner described above, and the rod 30 is rotatably indexed another 120 degrees. The grinding process is then repeated to form the third surface 19 of the instrument. The rod 30 may then be severed by conventional techniques, such as by axially advancing the rod and then moving the grinding wheel laterally through the rod. The severed rod is then further processed in a conventional manner to form the completed instrument as illustrated for example in FIG. 1.

As a modification of the illustrated process, the rod 30 may be initially severed into appropriate lengths, and each length may be separately mounted in a collet at the forward end of the indexing block 34, and then machined in the manner described above.

The process as described above has been found to produce instruments of consistently high quality, and at commercially acceptable production rates. Of particular significance, the process results in the formation of cutting edges at the apices of the triangular cross section, which are sharp, and substantially free of burrs and rolled edges which characterized the early instruments of titanium alloys as described above.

While an instrument of triangular cross section is illustrated in FIGS. 1–3, it will be a understood that other configurations are possible. For example, the instrument could have four sides which form a square in cross section. In the embodiment of FIGS. 4-5, the working length 18' of the instrument is tapered and is composed of two helical flutes 21, 22 of arcuate configuration. To fabricate this embodiment, substantially the same procedure as described above is followed. However, the taper of the working length 18' is preferably initially formed on a separate grinding machine, and the tapered blank is then mounted on a machine as shown in FIG. 6, and the axis of the wheel 38 is oriented so that the wheel lies in a plane which follows the desired helical configuration of the flutes 21, 22. Also, the outer periphery of the wheel is curved in cross section as opposed to being flat, and so as to form the desired arcuate configuration of the flutes 21, 22. Since the instrument as illustrated has two flutes, the rod is indexed 180° between the two machining operations.

In the drawings and specification, there has been set forth preferred embodiments of the invention, and although specific terms are employed, they are used in a generic and descriptive sense only and not for purposes of limitation.

That which is claimed is:

1. An endodontic instrument that is flexible and resistant to torsional breakage and that is adapted for use in performing therapy on a root canal of a tooth by rotating the instrument using a dental handpiece, said root canal having a sidewall, comprising:

an elongate shank composed of an alloy comprising at least about 40% titanium and having a diameter not greater than about 0.07 inches, said elongate shank further having a proximate end and an opposite pilot end so as to define a working length adjacent said pilot end, said shank having a fitting adapted to mate with the chuck of a dental handpiece;

at least one flute extending helically around said shank working length, so as to form axially adjacent flute segments; and a helical land positioned between said axially adjacent segments of said flute so as to reduce the tendency of the instrument to cut into the root canal sidewall and screw into the root canal as a result of rotation of the instrument by said dental handpiece.

2. The instrument according to claim 1, wherein said alloy comprises at least about 50% nickel.

3. The instrument according to claim 2, wherein said working length is tapered so as to form an included angle of between about ½ and 4 degrees.

4. The instrument according to claim 2, wherein said included angle is about 1 degree.

5. The instrument according to claim 2, wherein said included angle is less than about 1 degree.

6. The instrument according to claim 5, wherein said included angle is at least about ½ degree.

7. The instrument according to claim 2, wherein said included angle is greater than about 1 degree.

8. The instrument according to claim 7, wherein said included angle is not greater than about 4 degrees.

9. The instrument according to claim 1, wherein each of said axially adjacent flute segments are axially spaced apart by a pitch, and wherein said helical land has a width equal to at least 15% of said pitch.

10. The instrument according to claim 1, wherein said helical land has a width of at least about 0.005 inch.

11. The instrument according to claim 1, wherein said flute defines a curved concave wall when viewed in transverse cross section.

12. The instrument according to claim 1, wherein said at least one flute is a first flute and further comprising a second flute, said first and second flutes forming said axially adjacent flute segments.

* * * * *